United States Patent [19]

Kvaskoff

[11] Patent Number: Plant 6,909

[45] Date of Patent: Jul. 11, 1989

[54] ROSE PLANT KVAL

[76] Inventor: Michel Kvaskoff, 585L Chemin de Villebruc, 06560 Valbonne, Alpes Maritimes, France

[21] Appl. No.: 121,747

[22] Filed: Nov. 16, 1987

[51] Int. Cl.[4] ..... A01H 5/00

[52] U.S. Cl. ..... Plt./19

[58] Field of Search ..... Plt./11, 18, 19, 22, Plt./27, 28

[56] References Cited

PUBLICATIONS

Meikle, C. E. (1980) (Ed.) *Modern Roses* 8 (The American Rose Society; The McFarland Co., Harrisburg, Pa.) page xi cited.

(anon) *Manual of Classification* Documentation Organizations U.S. P.T.O. (1986) page PLT1.

*Primary Examiner*—James R. Feyrer

*Attorney, Agent, or Firm*—Young & Thompson

[57] ABSTRACT

A new, hybrid tea rose variety named 'Kval', which produces high centered, long lasting pink flowers of mild, fruity fragrance, 'Kval' is a product of crossing 'Mrs. George Delbard' with 'Millipost' as seed parent.

1 Drawing Sheet

The present invention relates to a new and distinct variety of rose plant.

The present invention provides a new variety of rose plant for the production of cut flowers and ornamental growing plants, which is an improvement on varieties of rose plants already cultivated. In particular, in accordance with the requirements of world-wide markets for cut flowers, the present invention provides a new variety of rose plant which has improved vegetative and reproductive qualities compared to varieties already cultivated, with a special color tone of the flowers, which is very much sought after and which permits the realization of maximum profit from the sale of the plants and their cut flowers.

After numerous attempts, it has been possible according to the present invention to produce a hybrid variety of rose plant, by crossing the variety known commercially as "Millipost" (varietal name) with the trademark "Omega", as the female plant, with a variety known commercially as "Mrs. George Delbard" (trademark), from "Deladel" (varietal name), as the pollenating plant, thereby to produce the first plant according to the present invention in which was embodied the desired characteristics.

The plant of the present invention may be easily reproduced and multiplied in any desired number having all the characteristics of the original plant, by means of vegetative multiplication methods of plants employed in floriculture and especially by grafting of shoots onto hose rose plants which are hardy in the soil where it is desired to cultivate the present invention.

Thus reproduced, the present invention transmits with constancy and fidelity all the distinctive characteristics to successive generations, thereby permitting the production of large homogeneous plant populations which are stable as to their characteristics. Thus the rose plant of the present invention is well adapted for industrial floriculture, for the production of cut flowers, or for plants destined for use in landscaping and gardening.

The characteristics which in their unique combination distinguish the rose plant variety according to the present invention and thus permit its ready identification, are set forth in the specification that follows, which in turn describes a group of plants industrially cultivated and grafted for about five years on Rosa Indica major growing in soil in greenhouses at Valbonne 06580, Alpes-Maritimes, France, and observed and described in the month of September.

Thus it is to this seasonable condition and these conditions of floriculture that reference must be made for purposes of comparison with the rose plant described hereinafter. It is of course to be understood that there will be normal fluctuations in the plant characteristics according to climate, soil and methods of culture, but these do not modify in any essential respect the present invention, as the repetition of the culture of the plant under the conditions described hereafter will permit ready identification of the plant according to the following characteristics.

The color nomenclature in the following description is in accordance with the tables in the reference "The Royal Horticultural Society" (hereinafter referred to as R.H.S.), except when the color is not described in that work, or when the nature of the color is sufficiently clearly indicated by ordinary usage.

Reference is also had to the accompanying photograph forming a part hereof, which shows various flowers in different conditions in bud and in bloom.

The characteristics are as follows:

Classification: Hybrid tea rose.

Derivation: "Millipost" crossed with "Deladel".

PLANT

Overall aspect: Upright to bushy, very vigorous, rapidly growing, very thin, erect and vertical. Vegetation tends to be bushy in the higher part of the plant.

Average height: 80 to 150 cm for full grown plants, cultivated under the indicated conditions. Principal stem averages 80 to 100 cm and sometimes more.

Roots: Of medium number and medium branches, extending deep into the soil, about 50 to 60 cm long and of a diameter at the top of about 2 to 10 mm. The bearded portions are long, of medium thickness and medium in number.

Principal stem: Of variable form and dimensions according to the species which receives the graft. In the described plants, the principal stem was constituted by the cutting of Rosa Indica major, 20 to 25 cm long and with a diameter at the base of 12 to 15 mm.

Principal branches: 4 to 8 in number, branching outward from the point of graft or from the base of other primary branches, somewhat divergent from the axis of the plant at their base, and then more vertical and parallel. Of medium thickness with little variation from the base to the top. The primary branches are articulated in sections 30 to 60 mm long whose joints are moderately differentiated, projecting somewhat from the branches.

The average dimensions of the principal branches are, as to length, from the base to the summit 50 to 100 cm, sometimes more, and as to average diameter 8 to 15 mm at the base. The bark of the principal branches is of medium thickness, smooth, glaborous, satiny and glossy in places.

The thorns are triangular, sharply pointed, differentiated in medium number and almost a right angle to the branches. The lower side of the thorns is concave while the upper side is straight or slightly convex. The thorns are more or less difficult to detach from the stems according to the season, and have average dimensions such that their average length is 3 to 10 mm and their average width 8 to 10 mm. Their thickness is 1 to 2 mm. The base of the thorns is elliptical with the largest part up. The small thorns, in medium number, have a length of 1 to 5 mm, a width of 1 to 3 mm, and a thickness of ½ to 1 mm, and are of the same shape as the large thorns. In color, the thorns are Greyed purple 184 B RHS. In texture, the thorns are robust, almost woody and rigid.

Floral branches: Average 3 to 5 in number on each primary branch, more numerous on the upper part of the primary branches and closely spaced (3 to 5 cm). In form, the floral branches are cylindrical, straight or slightly sinuous and sometimes slightly angled in correspondence to the nodes or joints, of medium thickness, and jointed into sections or internodes whose average length is 40 to 60 mm. The average dimensions of the floral branches or stems are 50 to 100 cm long to the base of the flower, and the average diameter, at the base, is 8 to 10 mm. The bark of the floral branches is smooth, glaborous, opaque or slightly satiny. The color of the floral branches is close to Green group 141 C RHS.

The thorns on the floral branches are numerous, generally large, intermixed with smaller thorns, scattered irregularly on the branches and more frequently on the lower parts of the branches. They average 5 to 10 per internode and are difficult to dislodge from the stem. The thorns are triangular, slightly concave on the lower side, sharply pointed, differentiated, slightly inclined downwardly. The base of the thorns is lanceolate and is larger in its upper part. The larger thorns have an average length of 10 mm, an average width of 10 to 12 mm and an average thickness of 1 to 3 mm. For the smaller thorns, the average length is 1 to 5 mm, the average width 3 to 6 mm, and the average thickness 1 to 2 mm. The color of the thorns is Greyed purple 184 B RHS. The texture of the thorns is rigid and resistant.

Leaves: Numerous on the primary branches and on the floral branches on which they are abundantly arrayed along all the lengths. The leaves are large and moderately elongated comprised by 3–5–7 leaflets inserted in opposed pairs plus a terminal leaflet on a stem which is thick at the base and elongated toward the end, at regular intervals. The average dimensions of the leaves are, on the primary branches, 100 to 130 mm in length and 90 to 140 mm wide. The leaves on the floral branches have an average length of 130 to 180 mm and an average width of 100 to 140 mm. The configuration of the leaves is somewhat bent, at various angles to the stems from almost a right angle or somewhat bent. The leaflets are flat in the foliate plane or slightly upturned relative thereto.

Leaflets: Limbus oval, elongated and wide, moderately sharp pointed at the end, little differentiated. Petiole short. The edges of the leaflets are dentate, the teeth being moderately numerous, simple, short and deeper adjacent the point of the leaflet. The average dimensions of the leaflets vary according to the state of development and according to the position on the stem, increasing from bottom to top and from the base of the stem toward the terminal leaflet.

The lower leaves, having 7 leaflets, have a first pair at the base of a length 18 to 20 mm and a width 8 to 12 mm; the second pair has a length 20 to 25 mm and a width 10 to 15 mm; the third pair a length 25 to 30 mm and a width 18 to 20 mm; while the terminal leaflet has a length 30 to 35 mm and a width 20 to 25 mm.

The leaves of five leaflets comprise a first pair having a length 28 to 30 mm and a width 20 to 25 mm; a second pair having a length 25 to 40 mm and a width 28 to 30 mm; and a terminal leaflet having a length 45 to 50 mm and a width 35 to 40 mm.

As to the medial and upper leaves, those having 7 leaflets have a first pair at the base whose leaflets are of a length 30 to 35 mm and a width 40 to 45 mm; a second pair having a length 40 to 45 mm and a width 25 to 30 mm; a third pair having a length 50 to 60 mm and a width 35 to 45 mm; and a terminal leaflet having a length 55 to 65 mm and a width 40 to 50 mm. The leaves having 5 leaflets may have a first pair at the base of a length 45 to 55 mm and a width 35 to 40 mm; a second pair having a length 55 to 65 mm and a width 40 to 50 mm; and a terminal leaflet having a length 65 to75 mm and a width 40 to 60 mm.

The surface of the leaves is, on the upper face, smooth, glaborous and moderately glossy. The under face is smooth, glaborous, opaque, with pennate and reticulated ribs that project moderately on the limbus.

In color, the upper face is of Green group 137 RHS and on the under surface of the Green group 138 B RHS.

In texture, the leaves are thick and resistant.

The stipules are straight and adnate along the stem for about ⅓ of the length of the first internode. The earlets are straight, pilose at the edges and moderately divergent from the stem.

FLOWER

Overall Aspect: The floral stem tends to be finer towards the end and to follow the light.

The flowering is almost continuous and its time of beginning is medium.

A single flower, erect, straight relative to and at the end of the stem, sometimes accompanied by several secondary floral buds which are smaller and shorter than the principal stem, carried by lateral stems inserted at the highest joints of the stems, which often will not have floral buds.

The flower pedicel has a medium number of hairs.

Closed floral bud: Conical, hemispheric at the base, surmounted by floriaceous appendices which are irregular and laciniated. Other lateral appendices are lanceolate and diverge from the contour of the bud. The opening of the sepals is moderately advanced relative to that of the petals. The average dimensions of the closed buds are 30 to 35 mm in length and 20 to 25 mm in diameter.

Partially opened bud: In the form of an urn widened at the top. The external petals open outwardly and are little if at all curled at their edges. The central petals are spiral and the center of the flower is closed, flat or a little raised. The average dimensions are 45 to 55 mm in length and 35 to 45 mm in diameter. The color is of Red purple group 63 C RHS at the base and Red purple group 63 b at the edges.

Calyx: Cup of medium dimensions, in the form of a hemisphere. Sepals are five in number, inserted on the edge of the cup, triangular, lanceolate and pointed, continuing off in foliaceous appendices with dentate and laciniated edges, of a length up to 25 to 35 mm and a width 5 to 20 mm. Other lanceolated and marginally dentated appendices diverge from the edges of the sepals. The average dimensions of the receptacle are 5 to 12 mm in length and 10 to 12 mm in diameter; and of the sepals 35 to 45 mm in length without the appendices and 5 to 6 mm wide at the base. The color of the upper surface is between Green group 138 D RHS and green group 138 A RHS. The color of the under face is between Green group 137 C RHS and Green group 137 D RHS. The surface of the upper face is covered with a fine white down. The lower face is smooth and opaque. In texture, the calyx is of moderate thickness and resistant.

Floral peduncle: Of medium length, straight, rigid, cylindrical, with small barbs of a length 0.5 to 1 mm which are tender. The medium length is 70 to 100 mm and the diameter 4 to 5 mm.

Open corolla: Very petalate, globose, with a raised center, and petals disposed in 30 to 50 superposed verticils. The shape is round, regular, and slightly star-shaped due to rounded or obtuse points formed by rolling of the petal edges. The petals swirl and curl moderately outwardly at the edges. The center of the flower is full and masks the stamens and the pistil. The profile of the flower is globose with the base petals slightly turned and rolled downwardly.

The average dimensions are, when completely open, 100 to 110 mm in diameter and 55 to 65 mm in length from the base of the cup to the tip of the petals.

The overall color is Red purple group 58 C RHS on the edge and Red purple group 58 D RHS toward the center.

The petals average 30 to 35 in number plus several petaloidal stamens at the center of the flower, inserted regularly in the cup. In shape, the external petals have a rounded limbus with lateral edges slightly convergent in a robust base which is differentiated. The outer edge is smooth, curved and moderately rolled outwardly, forming one or several obtuse points at the juncture of the rolls. The central petals have dimensions slightly smaller than the guard petals and are concave at the center and slightly rolled at the outer edges, sometimes with a slight crease. The base is large, differentiated, and robust. The average dimensions of the guard petals are 50 to 55 mm long and 45 to55 mm wide. The interior petals are 40 to 45 mm in length and 40 to 50 mm wide.

The color of the middle zone of inner side of the petal is Pink group 58 C RHS. The color of the marginal zone of inner side is Pink group 58 B RHS.

There is a spot at the base of inner side which size is small and which color is Yellow group 4 D RHS.

The color of the middle zone of outer side is Pink group 62 A RHS. The color of marginal zone of outer side is Pink group 63 B RHS.

There is a spot at the base of outer side, which size is small and color is Yellow group 4 D RHS.

The surface of the petals is, on the upper face, velvety with reticulated radial veins. The under face is satiny with veins slightly darker than the main color.

Reproductive organs: Stamens: Very numerous, predominantly pink, averaging 170 to 190, around the cup. The threads are thin, erect, slightly curved toward the center of the flower, and of a variable length from 5 to 10 mm. The anthers are of average dimensions, bisymmetrical, and terminated in threads. The styles are moderately numerous, at the center of the cup, surrounded by a bushy silky white down at their base. The styles range in length to 15 mm and are very thin, twisted, gathered at the base, free standing, purple and glandulous.

The stigmata are, situated above the anthers, fountain-shaped, terminated on the styles and yellowish. The ovaries are raised, partly out of the cup.

Fragrance: Moderately strong, with mildly fruity overtones.

Resistance of flowers to climate: Moderate

Resistance of flowers to shipment: Very good

Durability of cut flowers: Very good 10 to12 days

Resistance of the plant to cryptomgamic diseases: Not very good resistance to thrips. Resistance to oidium and mildew, same as Sweet Promise (varietal name), Sonia (trademark).

Special conditions for the examination of the variety: Under glass.

Ease of culture: Very good.

Compatibility with ordinary grafting stock: Very good.

Difference with the parent plant "Deladel": The color is different, the leaves are softer and the internodes are shorter.

Having described my invention, I claim:

1. The new and distinct variety of rose plant as described and illustrated.

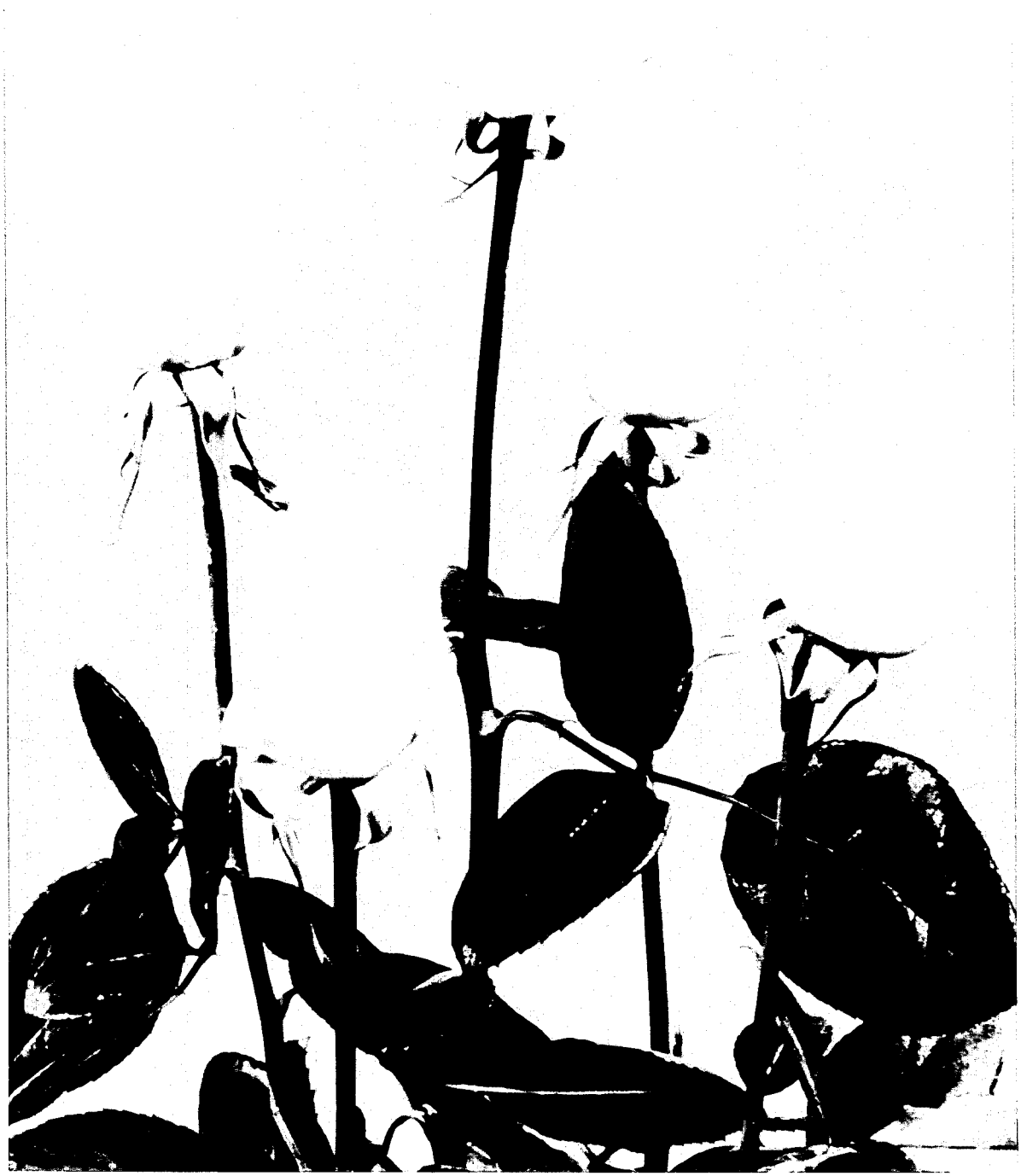

* * * * *